United States Patent [19]
Ostberg

[11] Patent Number: 5,750,106
[45] Date of Patent: May 12, 1998

[54] HUMAN MONOCLONAL ANTIBODIES TO CYTOMEGALOVIRUS

[75] Inventor: Lars G. Ostberg, Convent Station, N.J.

[73] Assignee: Novartis AG, Basel, Switzerland

[21] Appl. No.: 82,623

[22] Filed: Jun. 25, 1993

Related U.S. Application Data

[63] Continuation of Ser. No. 10,228, Jan. 28, 1993, abandoned.

[51] Int. Cl.$^6$ .................... A61K 39/42; C07K 16/08; C12N 5/24
[52] U.S. Cl. .................... 424/142.1; 424/147.1; 424/230.1; 435/339; 530/388.15; 530/388.3
[58] Field of Search .................... 424/85.8, 86, 89, 424/142.1, 147.1, 230.1; 435/70.21, 172.2, 240.27, 339; 530/388.15, 388.3, 389.4

[56] References Cited

U.S. PATENT DOCUMENTS

| | | | |
|---|---|---|---|
| 4,346,073 | 8/1982 | Aronson et al. | 424/86 |
| 4,491,632 | 1/1985 | Wands et al. | 435/240.27 |
| 4,574,116 | 3/1986 | Kaplan et al. | 435/68 |
| 4,608,337 | 8/1986 | Croce | 435/68 |
| 4,618,577 | 10/1986 | Handley et al. | 435/7 |
| 4,624,921 | 11/1986 | Larrick et al. | 435/172.2 |
| 4,634,664 | 1/1987 | Oestberg | 435/68 |
| 4,634,666 | 1/1987 | Engleman et al. | 435/68 |
| 4,716,104 | 12/1987 | Harris et al. | 435/5 |
| 4,743,562 | 5/1988 | Rasmussen et al. | 436/518 |
| 4,757,018 | 7/1988 | Brown | 435/240.2 |
| 4,783,399 | 11/1988 | Oldstone et al. | 435/5 |
| 4,818,678 | 4/1989 | Oldstone et al. | 435/5 |
| 4,950,595 | 8/1990 | Masuho et al. | 530/387 |
| 5,043,281 | 8/1991 | Masuho et al. | 435/240.27 |

FOREIGN PATENT DOCUMENTS

| | | |
|---|---|---|
| 0 248 909 | 12/1987 | European Pat. Off. . |
| 0 389 983 | 10/1990 | European Pat. Off. . |
| 2086937 | 5/1982 | United Kingdom . |
| WO 91/14703 | 10/1991 | WIPO . |
| WO 94/09136 | 4/1994 | WIPO . |
| WO 94/16730 | 8/1994 | WIPO . |

OTHER PUBLICATIONS

Ehrlich et al., "Rhesus Monkey Responses to Multiple Injections of Human Monoclonal Antibodies," *Hybridoma* 6(2):151–160, 1987.

Drobysky et al., "Phase I Study of Safety and PharmacoKinetics of a Human Anticytomegalovirus Monoclonal Antibody in Allogeneic Bone Marrow Transplant Recipients," *Transplantation* 51(6):1190–1196, Jun. 1991.

Aulitzky et al., "Human Monoclonal Antibodies Neutralizing Cytomegalovirus (CMV) for Prophylaxis of CMV Disease: Report of a Phase I Trial in Bone Marrow Transplant Recipients," *J. Inf. Disease* 163:1344–1347, 1991.

Dummer, "Cytomegalovirus Infection After Liver Transplantation: Clininical Manifestations and Strategies for Prevention", p. S767, Abstract, Reviews of Infectious Diseases, (1990) vol. 12, No. S7, pp. S767–S775.

Nokta et al., "Human Monoclonal Anti–Cytomegalovirus (CMV) Antibody (MSL–109): Enhancement of in vivo Foscarnet Induced Inhibition of CMV Replication", Abstract 100, Antiviral Research, (1992) vol. 19, No. S1, p. 97.

Stratta et al., "Cytomegalovirus Infection and Disease After Liver Transplantation. An Overview," p. 673, Abstract, Digestive Diseases and Sciences, (1992) vol. 37, pp. 673–688.

Capra et al., "The cross–reactive idiotype of A–strain mice" *Immun. Today* 3(12):332–339 (Dec. 1982).

Gaffar et al., "Variations in the Secretion of Monoclonal Antibodies by Human–Human Hybridomas" *Hybridoma* 5(2):93–105 (1986).

Ichimori et al., "Establishment of Hybridomas Secreting Human Monoclonal Antibodies Against Tetanus Toxin and Hepatitis B Virus Surface Antigen" *Biochem. Biophys. Res. Commun.* 129(1):26–33 (1985).

Kan–Mitchell et al., "Altered Antigenicity of Human Monoclonal Antibodies Derived from Human–Mouse Heterohybridomas" *Hybridoma* 6(2):161–172 (1987).

Kaye, J.F. et al., "Glycoprotein H of human cytomegalovirus (HCMV) forms a stable complex with the HCMV UL115 gene product" *J. Gen. Virol.* 73:2693–2698 (1992).

Maeda et al., "Production of Stable Mouse x Human Hybridomas Secreting HBs Antigen–Specific Human Monoclonal Antibody by Using In Vitro Sensitization" *Hybridoma* 5(1):33–41 (1986).

Meinart et al., "Mortality in patients with the acquired immunodeficiency syndrome treated with either foscarnet or ganciclovir for cytomegalovirus retinitis" *N. Engl. J. Med.* 326(4):213–220 (Jan. 23, 1992).

Newkirk, M.M. et al., "Complete Protein Sequences of the Variable Regions of the Cloned Heavy and Light Chains of a Human Anti–Cytomegalovirus Antibody Reveal a Striking Similarity to Human Monoclonal Rheumatoid Factors of the Wa Idiotypic Family" *J. Clin. Invest.* 81:1511–1518 (May 1988).

Palmer et al., "Production of Chinese Hamster Monoclonal Antibody to a Human Cell–Surface Antigen Using a Hamster–Human Somatic Cell Hybrid as Antigen" *Hybridoma* 5(3):249–253 (1986).

Protein Design Labs Press Release, "Protein Design Labs Announces Halt to One of Three Ongoing Clinical Trials in CMV Disease" Aug. 14, 1996 (3 pages).

(List continued on next page.)

*Primary Examiner*—Robert D. Budens
*Attorney, Agent, or Firm*—Townsend & Townsend & Crew LLP

[57] ABSTRACT

The present invention is directed to the human monoclonal antibody designated SDZ MSL 109 produced by the hybridoma cell line designated EV 2–7 having NCACC Accession No. 85 100 803. The human monoclonal antibody is specific for cytomegalovirus (CMV) and is useful as a therapeutic agent for treating CMV infections.

14 Claims, No Drawings

OTHER PUBLICATIONS

Protein Design Labs Press Release, "PDL Announces Updated Status of CMV Clinical Trials" Sep. 4, 1996 (3 pages).

Schrier et al., "Immune predisposition for cytomegalovirus retinitis in AIDS" *J. Clin. Invest.* 95:1741–1746 (Apr. 1995).

Simpson et al., "Neutralizing Monoclonal Antibodies that Distinguish Three Antigenic Sites on Human Cytomegalovirus Glycoprotein H have Conformationally Distinct Binding Sites" *J. Virol.* 67(1):489–496 (Jan. 1993).

Singer et al., "Foscarnet for Cytomegalovirus Retinitis" *Annals. Int. Med.* 103(6–part 1):962 (Dec. 1985).

Spaete, R.R., "Coexpression of Truncated Human Cytomegalovirus gH with the UL115 Gene Product or the Truncated Human Fibroblast Growth Factor Receptor Results in Transport of gH to the Cell Surfaces" *Virology* 193:853–861 (1993).

Tolpin et al., "Combination therapy of cytomegalovirus (CMV) retinitis with a human monoclonal anti–CMV antibody (SDZ–MSL–109) and either ganciclovir (DHPG) or foscarnet (PFA)" *IXth Intl. Conf. on AIDS* 9(1):54 Abstract No. WS–B11–2 (Jun. 1993).

Van Meel et al., "Human and Chimpanzee Monoclonal Antibodies" *J. Immun. Meth.* 80:267–276 (1985).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 369 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Homo sapiens ( i x ) FEATURE:
    ( A ) NAME/KEY: misc_feature
    ( B ) LOCATION: 1..369
    ( D ) OTHER INFORMATION: /standard_name= "Nucleotide
      Sequence of the V-h region of SDZ MSL 109"

( x i ) SEQUENCE DESCRIPTION: SEQ ID NO:1:

```
GAGGAGCAAG  TGCTGGAATC  TGGGGGAGGC  CTGGTCAAGC  CGGGGGGGTC  CCTGAGACTC    60
TCCTGTGCAG  CCTCTGGTTT  CACCTTCAGT  CCCTATAGCG  TCTTTTGGGT  CCGCCAGGCT   120
CCAGGAAAGG  GCCTGGAGTG  GGTCTCATCC  ATTAATAGTG  ATAGTACTTA  CAAATATTAC   180
GCAGACTCAG  TGAAGGGCCG  CTTCACCATC  TCCAGAGACA  ACGCCGAGAA  CTCAATATTT   240
CTGCAAATGA  ACAGCCTGAG  AGCCGAGGAC  ACGGCTGTTT  ATTACTGTGC  GAGAGATAGG   300
TCTTATTACG  CTTTTTCGAG  TGGTTCTTTG  TCGGACTACT  ACTACGGTCT  GGACGTCTGG   360
GGCCAAGGG                                                                369
```

( 2 ) INFORMATION FOR SEQ ID NO:2:

( i ) SEQUENCE CHARACTERISTICS:
    ( A ) LENGTH: 339 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
  ( A ) ORGANISM: Homo sapiens ( i x ) FEATURE:
  ( A ) NAME/KEY: misc_feature
  ( B ) LOCATION: 1..339
  ( D ) OTHER INFORMATION: /standard_name= "Nucleotide Sequence of the V-l region of SDZ MSL 109"

( x i ) SEQUENCE DESCRIPTION: SEQ ID NO:2:

```
GATATTGTGA TGACTCAGTC TCCACTCTCC CTGTCCGTCA CCCCTGGAGA GCCGGCCTCC      60
ATCTCCTGCA GGTCTAGTCA GAGCCTCCTG CATACTAATG GATACAACTA TTTGGATTGG     120
TACGTGCAGA AGCCAGGGCA GTCTCCACAG CTCCTGATCT ATCTGGCTTC TAATCGGGCC     180
TCCGGGGTCC CTGACAGGTT CAGTGGCAGT GGATCAGGCA CAGATTTCAC ACTGAAAATC     240
AGCAGAGTGG AGACTGAGGA TGTTGGGGTC TATTACTGTA TGCAAGCTCT ACAAATTCCT     300
CGGACGTTCG GCCAAGGGAC CAAGGTGGAA ATCAAACGA                            339
```

( 2 ) INFORMATION FOR SEQ ID NO:3:

( i ) SEQUENCE CHARACTERISTICS:
    ( A ) LENGTH: 123 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Homo sapiens ( i x ) FEATURE:
    ( A ) NAME/KEY: Peptide
    ( B ) LOCATION: 1..123
    ( D ) OTHER INFORMATION: /note= "The peptide sequence fo the V-h region of SDZ MSL 109."

( x i ) SEQUENCE DESCRIPTION: SEQ ID NO:3:

```
Glu Glu Gln Val Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Pro Tyr
            20                  25                  30

Ser Val Phe Trp Val Arg Gln Ala Pro Gly Lys Gly Leu Glu Trp Val
        35                  40                  45

Ser Ser Ile Asn Ser Asp Ser Thr Tyr Lys Tyr Tyr Ala Asp Ser Val
    50                  55                  60

Lys Gly Arg Phe Thr Ile Ser Arg Asp Asn Ala Glu Asn Ser Ile Phe
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Ala Phe Ser Ser Gly Ser Leu Ser Asp
            100                 105                 110

Tyr Tyr Tyr Gly Leu Asp Val Trp Gly Gln Gly
            115                 120
```

( 2 ) INFORMATION FOR SEQ ID NO:4:

( i ) SEQUENCE CHARACTERISTICS:
    ( A ) LENGTH: 113 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Homo sapiens ( i x ) FEATURE:
    ( A ) NAME/KEY: Peptide
    ( B ) LOCATION: 1..113
    ( D ) OTHER INFORMATION: /note= "The peptide sequence of the V-1 region of SDZ MSL 109"

( x i ) SEQUENCE DESCRIPTION: SEQ ID NO:4:

```
Asp Ile Val Met Thr Gln Ser Pro Leu Ser Leu Ser Val Thr Pro Gly
 1               5                   10                  15
Glu Pro Ala Ser Ile Ser Cys Arg Ser Ser Gln Ser Leu Leu His Thr
            20                  25                  30
Asn Gly Tyr Asn Tyr Leu Asp Trp Tyr Val Gln Lys Pro Gly Gln Ser
        35                  40                  45
Pro Gln Leu Leu Ile Tyr Leu Ala Ser Asn Arg Ala Ser Gly Val Pro
    50                  55                  60
Asp Arg Phe Ser Gly Ser Gly Ser Gly Thr Asp Phe Thr Leu Lys Ile
65                      70                  75                  80
Ser Arg Val Glu Thr Glu Asp Val Gly Val Tyr Tyr Cys Met Gln Ala
                85                  90                  95
Leu Gln Ile Pro Arg Thr Phe Gly Gln Gly Thr Lys Val Glu Ile Lys
            100                 105                 110
Arg
```

1

HUMAN MONOCLONAL ANTIBODIES TO CYTOMEGALOVIRUS

This is a continuation of application Ser. No. 08/010,228, filed Jan. 28, 1993, now abandoned.

BACKGROUND OF THE INVENTION AND INFORMATION DISCLOSURE

Infections with cytomegalovirus play an important role in morbidity and mortality of new born babies and of immune-suppressed patients, especially those having organ transplants, cancer and AIDS patients. Prevention of these infections by innoculation or a specific therapy of the infections was previously not possible. Only passive immunization with antibodies may be used prophylactically and therapeutically. Such antibody preparations are obtained from the serum of donors, who possess a high antibody titre to the virus as a result of an earlier infection. The disadvantage of such conventional antibody preparations is the limited number of suitable donors and the poor reproducibility or quality of the various preparations.

The development of hybridoma technology has made it possible today to produce antibodies of desired specificity in vitro, in large quantities and in invariable quality. Such antibodies are produced from hybridoma cells, that are cells which are obtained by fusing a myeloma cell with a lymphocyte which secretes antibodies of the desired specificity. There are three decisive factors for successful application of this technique:

1. The use of an appropriate myeloma cell, which immortalizes the resultant hybridoma and at the same time allows continuous production of the desired antibody in this cell.

2. Lymphocytes as fusion partners, which have been stimulated by suitable methods in vivo and/or in vitro to produce the desired antibodies.

3. The use of appropriate testing processes, with which the hybridoma cells which produce antibodies of the desired specificity may be selected.

The preparation of neutralizing human monoclonal antibodies to cytometalovirus is based on the correct combination of these three factors.

The invention thus relates to a process for the production of human monoclonal antibodies to cytomegalovirus (CMV), as well as these antibodies themselves and also the stable hybridoma line EV 2-7 used in this process, as well as its production.

Hybridoma cell lines and methods for producing them, as well as their use for producing antibodies are described in U.S. Pat. No. 4,634,664. These hybridoma cell lines are made by fusing a xenogeneic hybridoma cell to a genetically compatible substance producing cell.

Other references describing monoclonal antibodies include U.S. Pat. Nos. 4,574,116; 4,624,921; 4,491,632; 4,618,577; 4,608,377; 4,634,666; and 5,043,281; U.K. Patent Application 2,086,937A; European Patent Application 0,389,983; PCT Patent Application No. WO 91/14703; T. Maeder, et al., *Hybridoma*, Vol. 5, No. 1, pp. 33–41 (1986); Y. Ichimori, et al., *Biochemical and Biophysical Research Comm.*, Vol. 129, No. 1, pp 26–33 (1985); F. Van Meel, et al., *J. of Immunological Methods*, Vol. 80, pp 267–276 (1985); S. Gaffar, et al., *Hybridoma*, Vol. 5, No. 2, pp 93–105 (1986); D. Palmer, et al., *Hybridoma*, Vol. 5, No. 3, pp 249–253 (1986); and J. Kan-Mitchell, et al., *Hybridoma*, Vol. 6, No. 2, pp 161–172 (1987).

The safety and pharmacokinetic profiles of anti-cytomegalovirus monoclonal antibodies are discussed in W. E. Aulitzky, et al., *J. of Infections Diseases*, Vol. 163, pp 1344–1347 (1991) and W. Drobyski, et al., *Transplantation*, Vol. 51, No. 6, pp 1190–1196 (1991).

However, before the present invention, the anti-cytomegalovirus monoclonal antibody SDZ MSL 109 had not been derived or characterized. Thus, it is the object of the present invention to provide human monoclonal antibodies against cytomegalovirus and a method for producing and using same. It is a further object of the present invention to provide a process for the production of human neutralizing monoclonal antibodies to cytomegalovirus, characterized in that the myeloma cell SPAZ-4 is fused either with lymphocytes from human spleens, which already have an immune response to cytomegalovirus and have had secondary stimulation in vitro with a CMV antigen, or with peripheral blood lymphocytes from humans who have an increase in antibodies to cytomegalovirus, then the desired hybrid is selected, the hybridoma cell line thus prepared, which was filed on Oct. 9, 1985 at the National Collection of Animal Cell Cultures (NCACC) under number 85 100 803 is cultured in an in vitro medium, and the monoclonal antibody SDZ MSL 109 is isolated from this medium. It is an even further object of this invention to characterize monoclonal antibody SDZ MSL 109 and to provide for its usage for chronic illness or prophylactically.

SUMMARY OF THE INVENTION

This invention relates to human monoclonal antibodies effective against cytomegalovirus. It relates to the production of human neutralizing monoclonal antibodies to cytomegalovirus, characterized in that the myeloma cell SPAZ-4 is fused either with lymphocytes from human spleens, which already have an immune response to cytomegalovirus and have had secondary stimulation in vitro with a CMV antigen, or with peripheral blood lymphocytes from humans who have an increase in antibodies to cytomegalovirus, then the desired hybrid is selected, the hybridoma cell line thus prepared, which was filed on Oct. 9, 1985 at the National Collection of Animal Cell Cultures (NCACC) under number 85 100 803 is cultured in an in vitro medium, and the monoclonal antibody SDZ MSL 109 is isolated from this medium. The monoclonal antibodies are useful in treating immune-suppressed patients, such as new-borns and patients having cancer or organ transplants.

DETAILED DESCRIPTION

In accordance with the invention, the monoclonal antibodies to CMV are obtained by using the SPAZ-4 cell as the myeloma cell, prepared from drug resistant cell line SP-2 obtainable, e.g., from the NIGMS Human Genetic Mutant Cell Repository Ref. GM35669A (see U.S. DHHS 1982 Catalog of Cell Lines). Preparation of SPAZ 4 is summarized as follows. The SP-2 cell line is fused with normal human peripheral lymphocytes by conventional techniques. A large number of hybrids is obtained and, after approximately five weeks, clones are selected which show fast growth and no antibody production. These cells are selected for resistance to 8-azaguanine and with these it is possible to obtain mutants which are resistant to 20 μg/ml of 8-azaguanine. These cells are rendered sensitive to Hypoxanthine-Aminopterin-Thymidine (HAT) medium which showed that they had lost their ability to produce hypoxanthine phosphoribosyl transferase. One of these cell lines is SPAZ 4.

The lymphocytes stem from human spleens, for example, which have been removed due to traumatic rupture. Single cell suspensions are obtained from these spleens (within 2–4 hours following extirpation) and the lymphocytes are preserved in an appropriate freezing medium at −70° C. until fusion. Out of a number of spleens, those which stem from CMV-immune donors are chosen. This takes place by stimulating the cells with CMV-antigen, with subsequent measurement of the thymidine incorporation. Lymphocytes of spleens which are thus pre-selected are then stimulated in vitro over 7 to 14 days with CMV-antigen, and subsequently fused by known methods with the SPAZ-4 cell. Alternatively, the lymphocytes stem from blood samples taken from a human during a cytomegalovirus infection, if possible at the time of a titre increase of the cytomegalovirus antibodies. The lymphocytes are isolated from the blood by known methods and fused with SPAZ-4 cells. Hybrid cells were then selected by known methods (e.g. in HAT medium). The cell line obtained is then tested for the production of neutralizing antibodies to CMV. Positive cultures are subcloned and developed by in vitro culture over long periods of time into a stable cell line which produces neutralizing antibodies.

The stable hybridoma line, called EV 2–7 is thus obtained. [This cell line was deposited on Oct. 9, 1985 at the National Collection of Animal Cell Cultures (NCACC) PHLS Center for Applied Microbiology and Research, Division of Biologics, Porton Down, Salisbury, Wiltshire SP4 OJG, U.K., under Number 85 100 803.] This cell line produces neutralizing monoclonal antibodies, which may be obtained in any quantity, and, after purification by known methods, are available for the therapy and prophylaxis of CMV-infection in humans. The antibodies belong to the sub class IgG1 and possess a kappa chain as the light chain. The antibodies neutralize in vitro a series of tested strains of cytomegalovirus, including 3 laboratory strains (Towne, A D 169 and Davis), as well as a series of tested fresh clinical isolates. The antibodies bind protein A and may thus be purified from the culture supernatants by affinity chromatography on protein A sepharose.

The monoclonal antibodies produced from the hybridoma lines, especially SDZ MSL 109 have only slight or even no immunogenicity. This could be proved on monkeys. Because of the great similarity between the immunoglobulins of rhesus monkeys and that of humans, the rhesus monkey is a good animal model. It has been shown that the intravenous administration of 0.5 mg/kg body weight of the antibody to 3 monkeys (6.1 to 7.3 kg body weight, 12 administrations per animal over a period of 200 days) has not brought about any ascertainable immune response, especially no immune response through anti-idiotypic antibodies, since SDZ MSL 109 antibodies could be detected in the serum over several weeks (up to 180–250 days), and the pharmacokinetics did not correspond to that expected in the case of an immune response.

Furthermore, the antibodies remain in the blood stream for an extraordinarily long time: the half-life of the SDZ MSL 109 antibody measured in an ELISA test was 18 days ("Sandwich Assay": anti-SDZ MSL 109 idiotype goat immunoglobulin adsorbed onto synthetic material; detection of the bound SDZ MSL 109 antibody with rabbit-anti-SDZ MSL 109 idiotype with anti-rabbit goat-IgG, which is conjugated with horse-radish peroxidase). This should correspond in the case of humans to a half-life of at least 25 days (Schultze, H. E. and J. F. Heremans, *Molecular Biology of Human Proteins with Special Reference to Plasma Proteins*, Vol. I, Elsevier Publishing Co., New York, page 480 [1966]).

These findings are surprising: they show that it is not expected for the monoclonal antibodies according to the invention to bring about the formation of anti-idiotypic antibodies in humans. They may therefore be administered in multiple injections over a long period, e.g. six to twelve times a year, whereby the antibody concentration in the blood may be kept for months above a value of about 1 μg/ml. Indeed, it can be expected that the antibody can be administered for the remainder of the patient's life, if medically indicated.

The monoclonal antibodies according to the invention are therefore suitable for therapeutical application even in the case of chronic illness, or for prophylactic application.

The following examples illustrate the invention more fully. The examples are intended in an illustrative sense and not a limitative sense.

EXAMPLE I

Characterization of the Parent Myeloma Cell Line

The parent myeloma cell line, SPAZ-4, is a mouse x human hybridoma. This cell was constructed by fusing the murine hybridoma SP2/0-Ag14 to peripheral blood lymphocytes obtained from a healthy adult human male. The SP2/0-Ag14 is isolated as a re-clone of SP2/HL-Ag which was derived from SP2/HLGK; the hybrid between a BALB/c spleen cell with anti-sheep red blood activity to the myeloma cell line P3X63Ag8. SP2/0-Ag14 does not synthesize or secrete any immunoglobulin chains, is resistant to 8-azaguanine at 20μg/mL and does not survive in hypoxanthine, aminopterin, thymidine (HAT) containing media. This cell line is freely available and has the ATCC number CRL1581. The cell line used was obtained from the University of Erlangen, Erlangen, Germany, (Prof. zur Hausen). The SP2/0-Ag14 cells were fused to human peripheral blood lymphocytes (PBL) isolated from heparinized blood by centrifugation on Ficoll-Plaque (Pharmacia, Uppsala, Sweden), by the following procedure: After washing in saline, the PBLs were fused to the 8-azaguanine resistant myeloma cell in a proportion of PBL:myeloma of 2:1.

The fusion was performed according to Galfre et al., *Nature*, Vol. 266, p 550 (1977) using as fusogen a 50% solution of PEG 4,000 (Roth, Karlsruhe, Germany) in serum free Dulbecco's MEM. The cells were seeded into flat-bottomed microtiter plates at a concentration equivalent to $10^6$ myeloma cells per ml in HAT-containing culture medium. The culture medium was Dulbecco's MEM containing 20% heat-inactivated (56° C., 30 min.) fetal bovine serum (FBS), 10% NCTC-109 and additional amino acids, insulin, pyruvate and oxaloacetic acid as described (3). After 4 days the medium was replaced with growth medium containing only HT and after 3 weeks the supernatants were tested by Elisa for the presence of human antibody.

A large number of cultures were found producing human antibody, but as expected they lost this capacity in the following few weeks. Several cell lines obtained in this way were chosen for back-selection in 8-azaguanine which was used at a concentration of 20μg/ml for 3 weeks. The cultures showed massive cell death but it was possible to recover rapidly growing cells that were also shown to die rapidly in HAT-medium. The best growing of these cell lines, named SPAZ-4, was selected for further work. This cell line has been shown by a sensitive Elisa test to produce neither mouse nor human immunoglobulin. This test was performed by adsorbing rabbit anti-mouse (or anti-human) immunoglobulin antibodies to an Immuno-plate (Nunc, Roskilde, Denmark). Dilutions of supernatants and detergent-lysed cells were incubated in the wells and after washing again, incubated with polyvalent horseradish peroxidase-conjugated rabbit antibodies to mouse (or human) immunoglobulin (Miles-Yeda, Rehovot, Israel). After incubation and washing, the bound enzyme was detected using 1,2-phenylenediamine dihydrochloride (Fluka, Buchs, Switzerland). Standards of murine and human immunoglobulin showed this test to be sensitive into the low ng/ml range, but neither murine nor human immunoglobulin chains could be found in the SPAZ-4 materials. The SPAZ-4 cell line has been repeatedly shown to be free of mycoplasma contamination and is routinely being maintained in antibiotics-free medium to eliminate the risk of undetected contaminations.

EXAMPLE II

Preparation and Identification of Antibody SDZ MSL 109

The immune cell was obtained by in vitro immunization of human spleen cells. The spleen was obtained from an otherwise healthy motor vehicle accident victim undergoing surgery at the Landeskrankenhaus (County Hospital) Eisenstadt, Eisenstadt, Austria. The spleen was brought to the Sandoz laboratory in Vienna, Austria, within 4 hours after surgery and a single-cell suspension was cryopreserved in liquid nitrogen until used. In preliminary experiments the cells were shown to be stimulated in vitro by human cytomegalovirus (CMV) antigens. CMV antigen for in vitro stimulation was prepared from MRC-5 cells infected with the Towne strain of CMV. When the culture showed a complete cytopathic effect (CPE), the cells were scraped into the medium with a rubber-policeman, separated from the medium by centrifugation and washed 3 times in PBS. The cells from a 175 $cm^2$ tissue culture flask were then suspended in 1 ml of 0.1M glycine-NaOH, pH 9.5 and homogenized in a Dounce homogenizer. An equal volume of PBS was added and the suspension further homogenized by sonication for 30 seconds. Cell debris was removed by low speed centrifugation and the supernatant filtered through a 0.45 µm filter. The material was heated for 1 hour at 56° C., to inactivate potential residual infectivity, and stored at −70° C. until used.

Human spleen cells ($8 \times 10^7$) were cultivated in 50 ml RPMI 1640 containing 5% heat inactivated human serum and 2.5 µg/ml cimetidine. (The inclusion of cimetidine into the culture medium was based on suggestions in the scientific literature that cimetidine could inhibit the activity of T-suppressor cells, and should therefore be helpful in eliciting in vitro immune responses). After 3 days in culture the cells were centrifuged and resuspended in fresh medium containing CMV antigen at a final concentration of 1:100 (virus antigen batch VZ547). This concentration of antigen had been found to give optimum stimulation in initial screening experiments. After 7 days of culture in the presence of CMV antigen, $2 \times 10^7$ cells were harvested and fused with a similar number of SPAZ-4 cells using 50% PEG4000 as fusogen. The fused cells, at a concentration of $10^6$ cells/ml were seeded into flat-bottomed 96-well tissue culture microplates in the same culture medium, as described in Example I. In this case, however, only HT was in the medium and the aminopterin was added in an equal volume of medium after 24 hours. When an outgrowth of colonies with a hybridoma-like morphology could be observed, supernatants were assayed for human immunoglobulins by an Elisa-assay as described in Example I. Positive wells were then tested for neutralizing antibodies against CMV in a micro-neutralization assay. This test is performed by mixing 50 µl of the supernatant with 50 µl of a predetermined dilution of the virus for 1 hour at 37° C. After this incubation 25 µl of a dilution of guinea pig complement is added and the incubation is continued for 2 hours at 37° C. Tissue culture treated 96 well plates containing confluent monolayers of MRC-5 cells are aspirated until approximately 50µl of medium are left on the cells. 50 µl of the sample-virus-complement mix are added to the cells and incubated for 2 hours at 37° C., after which 100 µl of Eagle's MEM with 5% FBS are added.

The results are scored in an inverted microscope repeatedly over the following two weeks until a stable cytopathic effect (CPE) is obtained. Hybridoma cultures showing positive results in this test were picked and cloned by limiting dilution techniques in 96 well tissue culture plates in the same culture medium as mentioned above. When the clones had grown out, they were again tested for the capacity to produce antibodies that could neutralize CMV, and the positive clones were expanded and frozen in liquid nitrogen. One hybridoma obtained in this way was given the designation EV2-7; it produces the antibody SDZ MSL 109. The antibodies from this cell line have later been shown to neutralize the laboratory strains Davis and AD169 as well as 8 clinical CMV isolates tested. The neutralization capacity is highly dependent on the quality of the virus stock (if the virus preparation contains large amounts of non-infectious virus, this will absorb antibody and give a lower neutralization titer) but typically the antibody is able to neutralize the virus when present at a concentration of 100 ng/ml. The antibody was identified by a neutralizing test using complement but later studies have shown that there is no requirement for complement for neutralization.

The hybridoma cell has regularly been grown in bulk culture in a medium composed of Dulbecco's MEM containing 5% heat-inactivated (56° C., 30 min.) fetal bovine serum (FBS). In a long term effort it was attempted to grow the cells with less serum, with the ultimate goal of completely eliminating the serum. Many types of "serum-free" media exist commercially, but such products always contain added proteins, e.g. transferrin, albumin and growth factors e.g. insulin. Such media offer limited advantages over serum containing media, particularly regarding purification, but they still require validated testing of the proteinaceous raw materials and tests proving that the proteins have been removed from the final product. "Serum-free" media have only a small, if any, cost advantage over FBS-containing media. Therefore, the goal of the effort to remove the serum was to eliminate it without replacing it with some other proteinaceous additive. The cells were grown at ever decreasing concentrations of serum, but it was not possible to maintain viability and productivity when the serum concentration was under 1%. A major break-through, however, came with a method of using a high concentration of Fe+++ in the medium, and to make up the medium as a 1:1 mixture of Dulbecco's MEM and Ham's F12 (this medium also contains 17.3 µg/L of sodium selenite). It is important how the iron additive is added: from a stock solution of 0.1M Ferric Nitrate and 0.2M Sodium Citrate, 0.5 ml is added to each liter of medium, giving a final added concentration of 50 µM of Fe+++ (the basic medium contains approximately 0.12 µM of Fe+++). It seems that this high ferric ion concentration overrides the need for bringing iron to the growing cells by the transferrin-transferrin receptor mechanism. Even in this medium, however, the cells need time to adapt to lower serum levels, but eventually the serum can be completely eliminated, and the cells can still grow for unlimited periods of time. It has still not been reproducibly possible to clone the cells in the absence of serum, since high cell density seems to be a requirement for proliferation.

As described above, antibody SDZ MSL 109 was primarily identified based on its capacity to neutralize cytomegalovirus activity in vitro. The reason for using such a laborious method, rather than a simple binding assay, was our experience that antibodies binding strongly to cytomegalovirus infected cell lysates are primarily directed against the capsid protein and do not have any neutralizing capacity. Antibody SDZ MSL 109 has only a very weak activity in Elisa tests on cytomegalovirus infected cell lysates. The antigen used in such a binding study is prepared essentially as the stimulation antigen preparation described above, except that the antigen preparation is solubilized by a detergent (TRITON X-100). The antigen is adsorbed to an immunoplate and after washing away surplus antigen, dilutions of the antibody are incubated in the wells. After washing bound antibody is indicated by a horseradish peroxidase conjugated goat anti-human immunoglobulin reagent. The antibody has also been tested on a mock-infected antigen preparation and is completely negative in such a system. Attempts have been made to identify the antigen recognized by antibody SDZ MSL 109. Methods used include Western blots under reduced and non-reduced conditions, immunoprecipitation of radio-labeled infected cells and affinity chromatography on columns with coupled antibody. We have been able to identify a 82,000 dalton component by immunoprecipitation from a lysate of $^{35}$S-methionine labelled, CMV-infected MRC-5 fibroblasts. This protein is identical to the previously described gH glycoprotein of CMV.

The antibody SDZ MSL 109 is of the IgG1, Kappa type. To show that the antibody is of Kappa type is achieved with a slight modification of the immunoglobulin-Elisa described above, by replacing the polyvalent horse-radish peroxidase conjugated rabbit antibodies against human immunoglobulin with a reagent specifically identifying Kappa-chain determinants respectively. Very reliable reagents able to distinguish such sub-groups are commercially available, e.g. from Tago, Inc., Burlingame, Calif. The determination of the heavy chain subclass is easily achieved by using a panel of murine monoclonal antibodies identifying all four human IgG-subclasses. The reagents used are for IgG1: JDC1 (Southern Biotechnology Associates, Birmingham, Ala.), for IgG2: HP6002 and HP6014, for IgG3: HP6047 and HP6050, for IgG4: HO6023 and HP6025 (all from the University of Texas Health Science Center at Houston, Dr. Robert G. Hamilton). The identification is done by adsorbing SDZ MSL 109 to an immunoplate, incubating with a suitable dilution of the anti-subclass monoclonal antibody, and detecting binding with a goat anti-mouse Ig reagent. In such an experimental setting, SDZ MSL 109 gives a strong reaction with the anti-IgG1 reagent, but not with any of the others.

Preparations of SDZ MSL 109 are definitively negative when tested in sensitive Elisa tests for human immunoglobulin heavy chain classes other than IgG (IgM, IgA, IgD, and IgE have been tested) or for X-chain determinants. The pattern on a reduced SDA-PAGE gel shows that both the heavy and light chains appear as narrow, homogenous bands on the high resolution, silver stained gels. Isoelectric-focusing gels show 4 bands which is well in agreement with a homogenous immunoglobulin product, when one takes into consideration the micro-heterogeneity always seen in protein preparations. This, taken together with the information on the parent myeloma cell line is proof that this hybridoma cell line has no concurrent production of additional light or heavy chains.

EXAMPLE III

Purification of the Monoclonal Antibody

The monoclonal antibody SDZ MSL 109 is produced in cell culture from a hybridoma cell line in the absence of serum. This means that we have a need to remove from the final product only components from the cellular material. As SDZ MSL 109 is a human monoclonal antibody, which is not in itself expected to be immunogenic, it becomes very important to remove all potentially immunogenic components. The goal of the purification procedures is a final product that is more than 99.9% pure.

Even though most of the cells in the reactor are retained by the microspheres, a sizable number of cells are present in the harvested supernatant. To avoid gross contamination of the medium by cell components the supernatant is filtered through a polyvinylidene difluoride 0.65 µm Prostack/filter (Millipore), immediately after removal from the harvest tank. This type of filter unit works in a tangential flow mode which allows filtration of large amount of particulate material without clogging the filter. The cleared medium is collected into a refrigerated stainless steel tank.

The conditioned medium is concentrated using a nominal 30,000 dalton polysulfone spiral wound membrane supplied by Millipore Corporation. After concentration, the pH is set to 7.0 using 1M acetic acid. The material is sterile filtered through a Sartobran-PH 0.8/0.2 µm (Sartorius) filter (the 0.8 µm component is polyester, the 0.2 µm component is cellulose acetate) before being stored at 4° C. The material is microfiltrated (0.22 µm, Millipore) and filled into polypropylene shipment vessels. The purification step utilizes the high affinity of the human IgG1 antibody to Staphylococcus Aureus Protein A. The Protein A is purchased already coupled covalently by an amide bond to agarose. After packing the gel in a column, the column with its contents and attached tubing is sanitized by treatment with 70% ethanol in water for 24 hours (this may be changed to a 1.0N NaOH sanitization). The column is then equilibrated with PBS, pH 7.0. This treatment does not in any way damage the Protein A or the agarose particles.

Performing the affinity chromatography separation on the Protein A column involves the following sequential steps:

A/Loading. The concentrated conditioned medium is loaded on the column with a pump. The effluent from the column is collected and monitored for the presence of antibody by the human immunoglobulin ELISA. The column is loaded to such a degree that a measurable amount of antibody-containing fluid passes through the column. This allows a maximum utilization of the column material. The overload fraction is separately recovered and recycled if it contains more than 20 mg/ml of SDZ MSL 109.

B/Washing. To remove unbound materials the column is extensively washed with phosphate buffered saline, pH 7 with sodium chloride added to a final concentration of 0.5M. This wash is followed by a second washing step using a buffer of 0.02M sodium citrate, pH 5.6, containing 0.5M sodium chloride. This wash releases small amounts of the human antibody.

C/Elution. The bound monoclonal antibodies are eluted from the column using a buffer composed of 0.02M sodium citrate, pH 3.0, containing 0.5M sodium chloride. The eluted material is continuously diluted into a volume of 1M Tris-HCl, pH 8.0 to rapidly restore near-neutral conditions.

The Protein A purification is performed in a closed system utilizing a Waters 650 Protein Purification System which consists of the following equipment. The system is controlled by the Waters 600E System Controller. The pumping system consists of two 400 µl pump heads for flow rates up to 80 ml/min. The absorbance is monitored by a Waters 440 Absorbance Detector. An ISCO Model 2150 Peak Separator with Threshold can be used to detect and isolate peaks using a 6 port pneumatic valve for diversion of the fluid stream, alternately the separations can be performed by time based valve switching, controlled by the 600E Controller. The pH is monitored utilizing an in-line probe and a JENCO Model 6071 pH meter. Signals are sent from the pH meter and absorbance detector to a ABB Goerz Model SE120 recorder for recording of the chromatogram and pH changes. The Protein A is packed in a Pharmacia BPG 100/500 Bioprocess column. All buffer changes, and redirectioning of the effluent from waste pool to wash pools and elution pool is controlled by solenoid valves. The gel is packed between two adjustable adaptors which allows the column to be used without any mixing volume on top of the gel. This means that the buffer changes occur very abruptly and with a minimal mixing between different buffers. The performance of the column is monitored by an UV-monitor directly in the effluent from the column. The column should be able to bind at least 10 mg of SDZ MSL 109 per ml of gel.

In order to make the next purification step more effective and convenient, the eluate from the Protein A column is concentrated to at least 5 mg/ml SDZ MSL 109 using the same type of Pyrosart unit described above. The concentrate is sterile filtered through a 0.2 µM filter (Nalgene or Corning) and the sterile concentrate is stored at 4° C. until sufficient materials have been collected for the next purification step.

The antibody preparation is run on a Sephacryl S-300 High Resolution (Pharmacia) gel, packed in a Pharmacia BP 113/120 column with a bed volume of approximately 10 liters.

The column is packed in Lactated Ringer's Irrigation USP (Travenol Laboratories). The elution of the column is monitored by a Waters 650 Protein Purification System. The system is composed of the same equipment as the Protein A Purification System, without the pH meter.

The purpose of this step is not principally additional purification, but buffer change. After the elution of the Protein A column the antibodies are in a complex, hypertonic buffer composed of sodium citrate, sodium chloride and Tris-HCl. This buffer mixture can not be used directly as a vehicle for an intravenous injection. The buffer after this step is suitable both for intravenous injection and for long term refrigerated storage.

Even after the Protein A chromatography, which removes the bulk of DNA present in the concentrated supernatant, and the Sephacryl S-300HR which removes DNA molecules that are either significantly larger or significantly smaller than the monoclonal antibody product, there is a small, but detectable, presence of DNA in the antibody preparation. We have elected to remove this contaminant by an ion exchange step on a strong anion exchanger: Q Sepharose (Pharmacia Inc.). At the pH of Lactated Ringer's solution, antibody proteins have a positive charge, and are repelled by the anion exchanger. Nucleic acids, however, have a negative charge at this pH, and will bind to the column.

The column was packed according to the manufacturer's suggestions. After decanting the 20% ethanol solution the gel is delivered in, 100 m of gel was suspended in 200 ml of Lactated Ringer's solution. The slurry is poured into a Pharmacia K50/30 column, and when the gel has packed itself to a constant volume, it is sanitized with 1 column volume of 0.5N sodium hydroxide, followed by 3 column volumes of Dulbecco's PBS, followed by 5 column volumes of Lactated Ringer's solution. Immediately prior to use the column was washed with an additional 5 column volumes of Lactated Ringer's solution. The sample is then passed through the column and the pass-through is collected in a sterile container.

EXAMPLE IV

Molecular Analysis of SDZ MSL 109

SDZ MSL 109 was sequenced using standard techniques as follows:

To sequence the DNA, a CDNA library was prepared, using standard methodology, from hybridoma mRNA, in phage lambda zap (Stratagene, Inc.) The cDNA library was screened with an isolated human kappa constant region, or a human IgG1 constant region, probes. DNA fragments of an appropriate size were selected from BAM HI-digested cDNA on an agarose gel and cloned into bacteriophage lambda EMBL4. Phage plaques were screened with the respective probes, and positive clones were cloned into bacteriophage M13mp18 for nucleotide sequencing. Sequencing was done according to Maniatis et al. (Maniatis, T., Fritsch, E. F., and Sambrook, J., Molecular cloning: A laboratory manual. Cold Spring Harbor Laboratory, Cold Spring Harbor, N.Y.)

Method used to determine protein sequence: The DNA sequence was translated into protein sequence using the IntelliGenetics, Inc., software for VAX/VMS.

The DNA sequences for the $V_H$ and $V_L$ regions of SDZ MSL 109 are given below as Sequence No. 1 (SEQ ID NO:1) and Sequence No. 2 (SEQ ID NO:2), respectively. The peptide sequences for the $V_H$ and $V_L$ regions are given below as Sequence No. 3 (SEQ ID NO:3) and Sequence No. 4 (SEQ ID NO:4), respectively.

Sequence No. 1

(SEQ ID NO:1)

```
GAGGAGCAAGTGCTGGAATCTGGGGGAGGCCTGGTCAAGCCGGGGGGGTCCCTGAGACTC
TCCTGTGCAGCCTCTGGTTTCACCTTCAGTCCCTATAGCGTCTTTTGGGTCCGCCAGGCT
CCAGGAAAGGGCCTGGAGTGGGTCTCATCCATTAATAGTGATAGTACTTACAAATATTAC
GCAGACTCAGTGAAGGGCCGCTTCACCATCTCCAGAGACAACGCCGAGAACTCAATATTT
CTGCAAATGAACAGCCTGAGAGCCGAGGACACGGCTGTTTATTACTGTGCGAGAGATAGG
TCTTATTACGCTTTTTCGAGTGGTTCTTTGTCGGACTACTACTACGGTCTGGACGTCTGG
GGCCAAGGG
```

-continued

Sequence No. 2
(SEQ ID NO:2)

GATATTGTGATGACTCAGTCTCCACTCTCCCTGTCCGTCACCCCTGGAGAGCCGGCCTCC
ATCTCCTGCAGGTCTAGTCAGAGCCTCCTGCATACTAATGGATACAACTATTTGGATTGG
TACGTGCAGAAGCCAGGGCAGTCTCCACAGCTCCTGATCTATCTGGCTTCTAATCGGGCC
TCCGGGGTCCCTGACAGGTTCAGTGGCAGTGGATCAGGCACAGATTTCACACTGAAAATC
AGCAGAGTGGAGACTGAGGATGTTGGGGTCTATTACTGTATGCAAGCTCTACAAATTCCT
CGGACGTTCGGCCAAGGGACCAAGGTGGAAATCAAACGA

Sequence No. 3
(SEQ ID NO:3)

EEQVLESGGGLVKPGGSLRLSCAASGFTFSPYSVFWVRQAPGKGLEWVSSINSDSTYKYY
ADSVKGRFTISRDNAENSIFLQMNSLRAEDTAVYYCARDRSYYAFSSGSLSDYYYGLDVW
GQG

Sequence No. 4
(SEQ ID NO:4)

DIVMTQSPLSLSVTPGEPASISCRSSQSLLHTNGYNYLDWYVQKPGQSPQLLIYLASNRA
SGVPDRFSGSGSGTDFTLKISRVETEDVGVYYCMQALQIPRTFGQGTKVEIKR

---

What is claimed is:

1. A monoclonal antibody having peptide SEQ ID NO:3 for its $V_H$ region and peptide SEQ ID NO:4 for its $V_L$ region.

2. The monoclonal antibody of claim 1 characterized in that said antibody belongs to the subclass IgG1.

3. The monoclonal antibody of claim 1 characterized in that said antibody possesses a kappa chain as the light chain.

4. The monoclonal antibody SDZ MSL 109 produced by the EV-2-7 cell line assigned Accession Number 85 100 803 at the National Collection of Animal Cell Cultures.

5. A cell line producing the antibody of claim 1.

6. A pharmaceutical composition for treatment of a cytomegalovirus (CMV) viral infection, comprising a human anti-CMV antibody which binds to a CMV gH glycoprotein and neutralizes CMV, the antibody comprising a human immunoglobulin heavy chain having a variable region sequence of SEQ ID NO:3 and a human immunoglobulin light chain having a variable region sequence of SEQ ID NO:4.

7. A pharmaceutical composition according to claim 6, having an injection dosage of 0.5 mg/kg of body weight.

8. A pharmaceutical composition according to claim 6, wherein the anti-CMV antibody is an IgG1 isotype.

9. A pharmaceutical composition according to claim 6, wherein the antibody has a kappa light chain.

10. A pharmaceutical composition according to claim 6, wherein said human anti-CMV antibody is SDZ MSL 109.

11. A pharmaceutical composition according to claim 10, wherein said SDZ MSL 109 monoclonal antibody is produced by the hybridoma cell line designated EV-2-7 assigned Accession Number 85 100 803 at the National Collection of Animal Cell Cultures.

12. A pharmaceutical composition according to claim 11, wherein the hybridoma produces the heavy chain from DNA having the sequence of SEQ ID NO:1.

13. A pharmaceutical composition according to claim 11, wherein the hybridoma produces the light chain from DNA having the sequence of SEQ ID NO:2.

14. A method for treating a CMV viral infection in a patient, said method comprising the step of administering a pharmaceutical composition according to claim 6.

* * * * *